United States Patent [19]

Hytönen

[11] Patent Number: 5,663,332
[45] Date of Patent: Sep. 2, 1997

[54] METHOD FOR THE PREPARATION OF 3-HYDROXY-5-[2-(DIMETHYLAMINO)ETHYL]-2,3-DIHYDRO-2-(4-METHOXY-PHENYL)-1,5-BENZOTHIAZEPINE-4(5H)-ONE

[75] Inventor: Martti Hytönen, Espoo, Finland

[73] Assignee: Orion Corporation Fermion, Espoo, Finland

[21] Appl. No.: 528,839

[22] Filed: Sep. 15, 1995

[30] Foreign Application Priority Data

Sep. 16, 1994 [EP] European Pat. Off. ............ 94114643

[51] Int. Cl.⁶ .................... A61K 31/55; C07D 281/10; C07D 417/02
[52] U.S. Cl. ............................................................ 540/491
[58] Field of Search ............................................ 540/491

[56] References Cited

U.S. PATENT DOCUMENTS 3,562,257  2/1971  Kugita et al. ............................ 540/491

FOREIGN PATENT DOCUMENTS

| 0 081 234 | 6/1983 | European Pat. Off. | ............ 540/491 |
|---|---|---|---|
| 0 154 895 | 9/1985 | European Pat. Off. | ............ 540/491 |
| 0 320 361 | 6/1989 | European Pat. Off. | ............ 540/491 |
| 0 320 362 | 6/1989 | European Pat. Off. | ............ 540/491 |
| 0 338 892 | 10/1989 | European Pat. Off. | ............ 540/491 |
| 0 353 032 | 1/1990 | European Pat. Off. | ............ 540/491 |
| 0 424 214 | 4/1991 | European Pat. Off. | ............ 540/491 |
| 63-275572 | 11/1988 | Japan | ............ 540/491 |
| WO 91/17153 | 11/1991 | WIPO | ............ 540/491 |
| WO 92/10485 | 6/1992 | WIPO | ............ 540/491 |

OTHER PUBLICATIONS

Chemical Abstracts, vol. 115, No. 11, Sep. 16, 1991, p. 909, Abstract No. 114560f, "Preparation of high–Purity diltiazem from cis–=(+)–2,3–dihydro–3–hydroxy–2–(4–methoxyphenyl)–1,5–benzo=thiazepin–4(5H)–one Without Isolation of N–alkylated Intermediate", Inventors: Jiri Hrbata et al.

*Primary Examiner*—Robert T. Bond
*Attorney, Agent, or Firm*—Burns, Doane, Swecker & Mathis, L.L.P.

[57] ABSTRACT

A method for the preparation of 3-hydroxy-5-[2-(dimethylamino)ethyl]-2,3-dihydro-2-(4-methoxyphenyl)-1,5-benzothiazepine-4(5H)-one and use of the product prepared by this method for making pharmaceutical compositions and pharmaceutically active compounds is disclosed starting with N-alkylation of 3-hydroxy-2,3-dihydro-4-(methoxyphenyl)-1,5-benzothiazepin-4(5H)-one with a (dimethylamino)ethyl halide wherein the N-alkylation reaction is carried out in a reaction mixture comprising 2-butanone and water. The product of this reaction and its salts have utility as pharmaceutically active compounds and as intermediates for making pharmaceutically active compounds. The disclosed method and use is simpler, more efficient and safer than prior known methods and produces a product of superior purity.

13 Claims, No Drawings

METHOD FOR THE PREPARATION OF 3-HYDROXY-5-[2-(DIMETHYLAMINO)ETHYL]-2,3-DIHYDRO-2-(4-METHOXY-PHENYL)-1,5-BENZOTHIAZEPINE-4(5H)-ONE

This invention relates to a process for the preparation of 3-hydroxy-5-[2-(dimethylamino)-ethyl]-2,3-dihydro-2-(4-methoxyphenyl)-1,5-benzothiazepine-4(5H)-one and salts thereof, which may be used to make pharmaceutically active compounds such as cis-(+)-3-acetoxy-5[2-(dimethylamino)-ethyl]-2,3-dihydro-4-(methoxyphenyl)-1,5-benzothiazepin-4(5H)-one, which is hereinafter referred to as diltiazem. Diltiazem of formula (Ia) is used in cardivascular therapy and especially in the treatment of angina pectoris.

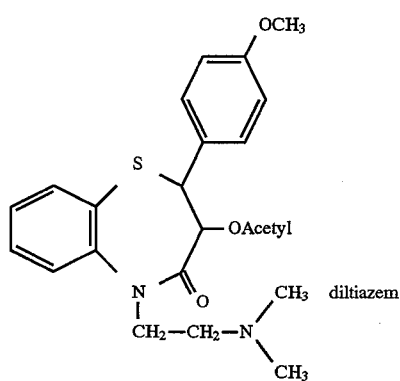

The manufacture of diltiazem has been described in the U.S. Pat. No. 3,562,257. In that method cis-(+)-3-hydroxy-2,3-dihydro-2-(4-methoxyphenyl)-1,5-benzothiazepin-4(5H)-one of formula (II)

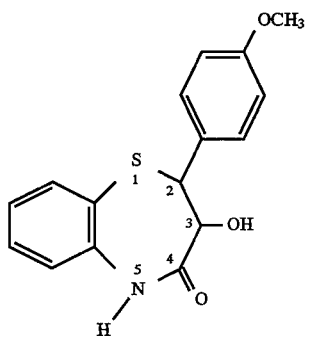

has been allowed to react with 2-(dimethylamino)ethyl chloride in the presence of a base such as sodium hydride, metallic sodium or sodium amide, in a solvent such as dimethylsulfoxide, dioxane, toluene or xylene to yield cis-(+)-3-hydroxy-5-(2-dimethylamino)ethyl-2,3-dihydro-2-(4-methoxyphenyl)benzothiazepin-4(5H)-one of formula (I)

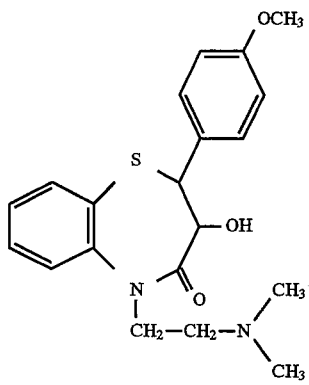

which has been reacted with acetic anhydride to make diltiazem.

In EP-A-0 081 234 another N-alkylation method is described. In this document, a process is disclosed for preparing either the benzothiazepine derivative (I) or diltiazem (Ia) by condensing either the compound of formula (II) to make the benzothiazepine derivative (I) or cis-(+)-3-acetoxy-2,3-dihydro-2-(4-methoxyphenyl)-1,5-benzothiazepine-4(5H)-one (IIa)

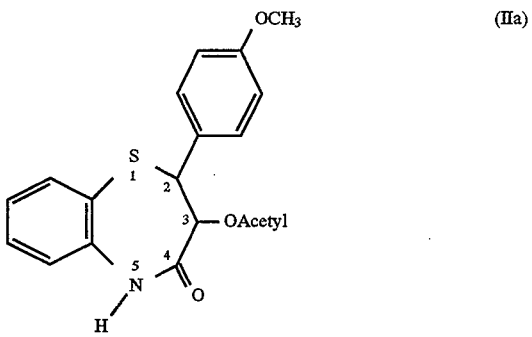

to make diltiazem (Ia), respectively, with 2-(dimethylamino) ethyl chloride in the presence of potassium hydroxide in acetone or in the presence of potassium carbonate in a solvent selected from acetone, lower alkyl acetate, a mixture of acetone and water and a mixture of lower alkyl acetate and water. This process has several disadvantages. In all of the methods described in the examples of EP-A-0 081 234, the desired product is isolated by crystallization as its hydrochloride salt from ethanol after complicated work-up process steps, in order to gain a pure enough product.

Additionally, because acetone is completely miscible with water, the normal removal of salts by washing with water is impossible. Thus, the solvent has to be removed first and changed to another solvent, such as toluene, which is subsequently changed after removal of salts to ethanol, from which the product can be crystallized and with which impurities can be removed. This is an uneconomic, time, energy and capacity consuming process.

All of the examples of EP-A-0 081 234 show that that process required 8 to 10 times the amount of solvent relative to the amount by weight of starting material and the reaction time varied from 3 hours to 30 hours, which makes the process expensive and capacity consuming.

Additionally, because ethyl acetate and methyl acetate hydrolyze under basic conditions, the regeneration and reuse of these solvents becomes quite difficult.

In the patent application WO092/10485, an alkylation reaction is described using toluene as solvent and potassium carbonate as base, with dimethylformamide or N-methylpyrrolidinone as an additional solvent. This reaction, however, requires a phase transfer catalyst for the completion of the reaction, which makes this system complicated and expensive.

An object of this invention is to provide a simple, economic and reliable method for the industrial manufacture of the pharmaceutically active benzothiazepine derivative of formula (I) and of diltiazem (Ia).

Another object of this invention is to provide a method whereby the pharmaceutically active benzothiazepine derivative of formula (I) and pharmaceutically active reaction products using the thus prepared compound (I) as starting product (intermediate), such as diltiazem (Ia), can be manufactured rapidly and with high productivity.

A further object of this invention is to improve occupational and environmental safety.

These and other objects of the invention are achieved by the invention as described in the appended claims.

One aspect of the invention is a process which comprises alkylating a benzothiazepine derivative of formula (II), which may be in the cis- or trans-form and have a (+) or (−) optical rotation, or a salt thereof, with 2-(dimethylamino) ethyl halide or a salt thereof in the presence of potassium carbonate or potassium hydroxide characterized in that the reaction is carried out in a reaction mixture comprising 2-butanone and water.

One advantage of this process of the invention is that the amount of organic solvent needed is far less than required in the known processes. In one embodiment of this invention, the amount by weight of 2-butanone used to conduct this reaction is only 1.3 to 1.9 times the amount by weight of the starting material.

Another advantage of this invention is that significantly smaller amounts of the very toxic and carcinogenic alkylating agent 2-(dimethylamino)ethyl halide, less than 1.2 mol per mol of benzothiazepine derivative (II), may be used in conducting the process according to this invention.

Yet another advantage is the high productivity of this method. In one embodiment, the time required for at least 90%, preferably at least 95%, conversion of the starting material to product generally varies from 50 minutes to 2.5 hours, and the reaction is preferably conducted within 50 minutes to 1.5 hours, often just depending on the amount of potassium hydroxide or potassium carbonate used.

A preferred amount range of 2-(dimethylamino)ethyl halide is 1.05–1.18 mol, especially 1.12 to 1.16 mol, per mol of benzothiazepine derivative (II). The halide of the 2-(dimethylamino)ethyl halide is preferably chloride.

A preferred amount of potassium carbonate or potassium hydroxide to be used in the above-mentioned process is in the range from 3 to 3.5 mol, especially 3.1 to 3.3 mol, per mol of benzothiazepine derivative (II).

A preferred amount of 2-butanone in the reaction mixture is in the range from 1 to 2, and more preferably from 1.3 to 1.9 and even more preferably 1.6±15%, times the amount by weight of benzothiazepine derivative (II).

The amount of water in the reaction mixture is preferably at least 0.4 mol (corresponding to about 9.8% water to 2-butanone (w/w)), more preferably at least 0.6 mol (corresponding to about 15% water to 2-butanone (w/w)) and even more preferably at least 0.7 mol or 0.8 mol (corresponding to about 17 or 20% water to 2-butanone (w/w)), per mol of 2-butanone. Most preferably the amount of added water is about 0.8 mol per mol 2-butanone (about 20% (w/w)). The maximum amount of water is not particularly limited, but in one preferred embodiment, the amount of water present during conversion of benzothiazepine derivative (II) to benzothiazepine derivative (I) is 0.9 mol or less per mol of 2-butanone (corresponding to about 22% water to 2-butanone (w/w) or less). An especially preferred range is from 0.7 to 0.9 mol per mol of 2-butanone.

It is preferred to carry out the reaction at the refluxing temperature of the reaction mixture, or preferably at a temperature in the range from 75° to 85° C. such as when the reaction is conducted at atmospheric pressure. The process can of course be conducted at a higher temperature when the pressure exceeds atmospheric pressure and, in a preferred embodiment, the benzothiazepine derivative (I), 2-(dimethylamino)ethyl halide, potassium hydroxide or potassium carbonate, and 2-butanone are combined and heated to an elevated temperature such as a temperature in the range from 40° to 85° C., preferably in the range from 50° to 65° C., before adding the water to the reaction mixture.

After the reaction, the salts may be washed away, such as by adding more water to the reaction mixture and then separating the aqueous phase from the organic product-containing phase. The reaction is very selective and no additional purification of the desired product thereof is needed.

This product, or a pharmaceutically acceptable salt thereof, has utility as an active ingredient in a pharmaceutical preparation for the treatment of coronary insufficiency and arterial hypertension as described in EP-A-0 154 895 and is furthermore useful as an intermediate in a process for the preparation of pharmaceutically active compounds such as the 2-phenyl-1,5-benzothiazepine derivatives having antihypertensive and vasodilating activity described in JP-A2-63-275572 and of diltiazem (Ia) which itself is useful in cardiovascular therapy and especially in the treatment of angina pectoris. The N-alkylation process of this invention is preferably carried out with a benzothiazepine derivative (II) having the appropriate cis- or trans-conformation corresponding to the required cis- or trans-conformation of the desired product (I). It is preferred to use a benzothiazepine derivative (II) having the cis(+)-configuration, i.e., the 2S,3S-isomer.

The alkylated product (I) is preferably isolated by simply removing, e.g., by distilling or evaporating, the 2-butanone from the organic product-containing phase which was isolated from the reaction mixture such as under atmospheric pressure or under reduced pressure (e.g., vacuum distillation). The 2-butanone removed from the reaction mixture may be reused in this process, which provides additional cost savings and avoidance of chemical waste disposal problems. The resulting product residue containing the benzothiazepine derivative (I) may then be subjected to crystallization, e.g., in the form of pharmaceutically acceptable salts and then be formulated as a pharmaceutical composition in a per se known manner or may subsequently be used as such as a chemical intermediate for making different pharmaceutically active compounds.

An important and surprising advantage of the present invention is the fact that the benzothiazepine derivative of formula (I) obtained after removal of the 2-butanone is of sufficient yield and purity as not to require isolation and/or purification by way of an extra crystallization step or some other form of purification if it is desired to use (I) as the starting compound of a further reaction. This permits one to add new reagents and solvents to the same vessel in which the 2-butanone was removed to convert the benzothiazepine derivative of formula (I) to another derivative such as diltiazem (Ia).

Therefore, another aspect of this invention is a process which comprises alkylating a benzothiazepine derivative (II) as described above and subsequently acylating the alkylated product (I) in the 3-position with an active reagent to give a pharmaceutically active compound (Ia').

The active reagent is a carboxyhalide, carboxylic acid anhydride, or activated ester derivative, or compound of the formula

$R^2$—Y—COOH  (III), or a salt thereof, wherein $R^2$ represents cycloalkyl, lower alkoxycarbonyl, COOH, lower alkanoyl, heterocyclyl, halogen atom, lower alkyl, lower alkoxy, aralkoxy, mono-, di- or trihaloalkyl, hydroxy, aryloxy, amino, acylamino, lower alkylthio, lower alkylsulfinyl, lower alkylsulfonyl, di-(lower alkyl)-aminosulfonyl, arylcarbonyl, lower alkoxycarbonyl, or phenyl which optionally may have 1 to 3 substituents and Y represents a bond, lower alkylene, lower alkenylene, or lower alkyleneoxy. The terms "lower alkyl", "lower alkylene", "lower alkoxy" etc. are meant to designate groups with 1 to 5, preferably 1 to 3, carbon atoms. The resulting reaction product from the reaction of (I) with the afore-mentioned active reagent is a the benzothiazepine of the formula (Ia')

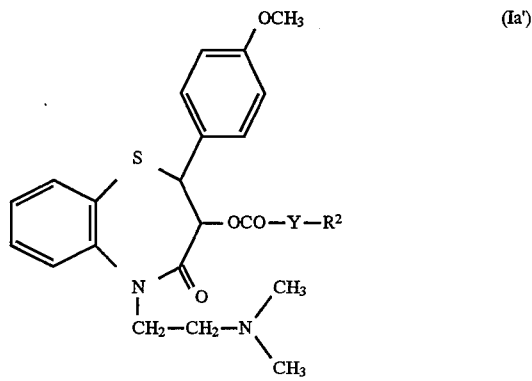

wherein the hydroxyl group in the 3-position is replaced by the substituent —OCO—Y—$R^2$ and wherein the substituents Y and R have the afore-mentioned meaning.

The reaction for making pharmaceutically active compounds using the benzothiazepine derivative (I) which has been prepared as described above as an intermediate (starting compound) can be conducted in situ in the same vessel in which the N-alkylation process of this invention was completed or in the same vessel in which 2-butanone was removed from the organic product-containing phase isolated from the reaction mixture obtained by conducting the N-alkylation reaction of this invention.

The pharmaceutically active compounds described in JP-A2-63-275572 may thus be prepared by first carrying out the afore-mentioned alkylation method to obtain the benzothiazepine derivative (I) and subsequently carrying out an acylation with the afore-mentioned active reagent.

In a preferred embodiment of this aspect of the invention, the compound (I) obtained via the N-alkylation process of this invention serves as an intermediate and is acetylated at the 3-position to produce diltiazem (Ia). Diltiazem (Ia) may be converted to the respective pharmaceutically acceptable salt, such as the hydrochloride salt, in the usual manner such as by extracting diltiazem with an appropriate organic solvent, such as toluene, and treating the extracted diltiazem with the appropriate acid to form the respective salt, such as with an ethanol-HCl solution to form the hydrochloride salt.

According to one preferred embodiment of the inventive process for making diltiazem (Ia), the alkylation of the benzothiazepine derivative of formula (II) is conducted with 2-(dimethylamino)ethyl chloride in the presence of potassium carbonate and a mixture of 2-butanone and water. After additional water is added to the reaction mixture for the removal of salts, the aqueous phase is separated from the 2-butanone phase and 2-butanone is removed, e.g., distilled off, for regeneration. Acetic anhydride is added to the residue and allowed to react with the benzothiazepine derivative of formula (II). After the acetylation reaction, an organic solvent such as toluene is added to the mixture and the desired product, diltiazem (Ia) HCl salt, is crystallized using an ethanol-HCl solution.

As mentioned herein, in comparison with the earlier known methods, the above-mentioned method of the present invention is clearly advantageous and more economical for the preparation of benzothiazepine derivative (I) and other benzothiazepine derivatives, such as diltiazem (Ia), especially, on an industrial scale. Several complicated work-up steps can be avoided using this novel method, much smaller amounts of solvent and toxic reagents can be used, which yields significantly less waste material and also offers occupational safety advantages, in addition to a much smaller need for equipment capacity and energy use.

A high yield of a product of superior quality is also an important advantage.

The following examples illustrate the present invention:

EXAMPLE 1

A mixture containing 40 g of cis-(+)-3-hydroxy-2,3-dihydro-2-(4-methoxyphenyl)-1,5-benzothiazepin-4(5H)-one, 21.9 g of 2-(dimethylamino)ethyl chloride hydrochloride, 57.5 g of potassium carbonate and 64 g of 2-butanone is heated to +58° C. and 12.8 ml water is added. Then the obtained mixture is refluxed at +82° C. at atmospheric pressure for 1.5 hours, after which 104 ml of water is added and the organic and aqueous phases are separated. 2-Butanone is distilled off the organic product-containing phase for regeneration and acetic anhydride is added to the distilled residue. After the reaction with acetic anhydride, the product diltiazem is extracted into toluene, from which it is then crystallized using an ethanol-HCl solution.

After the alkylation reaction, the obtained intermediate was not isolated, but its yield was determined in the following way: After removing 2-butanone, 50.5 g of the crude intermediate remained. As found with medium pressure liquid chromatography (MPLC), cis-(+)-3-hydroxy-5-[2-(dimethylamino)-ethyl]-2,3-dihydro-2-(4-methoxyphenyl)-1,5-benzothiazepine-4(5H)-one was obtained at a yield of 97.2%. The purity of the product of the alkylation reaction was confirmed by NMR spectroscopy.

EXAMPLE 2

A mixture containing 40 g of cis-(+)-3-hydroxy-2,3-dihydro-2-(4-methoxyphenyl)-1,5-benzothiazepin-4(5H)-one, 21.9 g of 2-(dimethylamino)ethyl chloride hydrochloride, 64 g of potassium carbonate and 64 g of 2-butanone is heated to +58° C. and 12.8 ml of water is added to the mixture, which is then refluxed for 50 minutes. 110 ml of water is then added and the aqueous phase is separated from the 2-butanone organic phase. The 2-butanone phase containing the product is used for the continuation of the process, as is described above in Example 1. The residue obtained after removal of 2-butanone by distillation was 50.23 g, which contained, according to MPLC, cis-(+)-3-hydroxy-5-[2-(dimethylamino)ethyl]-2,3-dihydro-2-(4-methoxyphenyl)-1,5-benzothiapine-4(5H)-one at a yield of 96.1%.

I claim:

1. A process for the preparation of a benzothiazepine derivative of the formula (Ia')

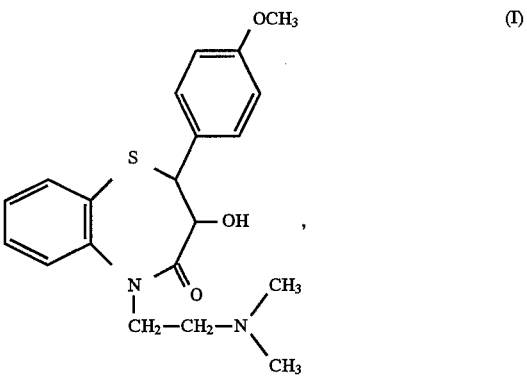

or a pharmaceutically acceptable salt thereof, by alkylating the benzothiazepine derivative of formula (II):

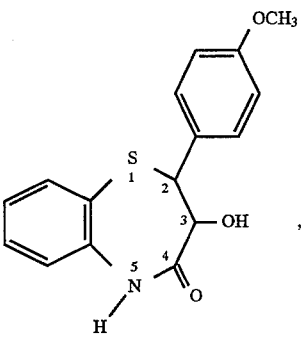

or a salt thereof, with a 2-(dimethylamino)ethyl halide, or a salt thereof, in the presence of potassium carbonate or potassium hydroxide wherein the alkylation is effected using a reaction mixture comprising 2-butanone and water in amounts ranging from 0.4 to 0.9 mol per mol of 2-butanone, and subsequently acylating the resultant 3-hydroxy-5-[2-(dimethylamino)ethyl]-2,3-dihydro-2-(4-methoxyphenyl)-1,5-benzothiazepine-4(5H)-one of the formula (I)

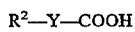

at the 3-position with an active reagent selected from the group consisting of carboxyhalide, carboxylic acid anhydride, activated ester derivative, and a compound of the formula

R²—Y—COOH (III)

or a salt thereof, wherein R² is selected from the group consisting of cycloalkyl, $C_1$-$C_5$ alkoxycarbonyl, COOH, $C_1$-$C_5$ alkanoyl, heterocyclyl, halogen atom, $C_1$-$C_5$ alkyl, $C_1$-$C_5$ alkoxy, aralkoxy, mono-, di- or trihaloalkyl, hydroxy, aryloxy, amino, acylamino, $C_1$-$C_5$ alkylthio, $C_1$-$C_5$ alkylsulfinyl, $C_1$-$C_5$ alkylsulfonyl, di-($C_1$-$C_5$ alkyl)-aminosulfonyl, arylcarbonyl, $C_1$-$C_5$ alkoxycarbonyl, and phenyl which is unsubstituted or may be substituted at 1–3 positions and wherein Y is selected from the group consisting of a bond, $C_1$-$C_5$ alkylene, $C_1$-$C_5$ alkenylene, and $C_1$-$C_5$ alkyleneoxy, wherein the acylation reaction is conducted in situ directly after conducting the alkylation reaction and removal of the water and 2-butanone from the reaction mixture, without an intervening purification or crystallization step between removal of the water and 2-butanone from the reaction mixture and the acylation reaction step.

2. The process of claim 1, wherein the acylated product (Ia') is converted into a pharmaceutically acceptable salt thereof.

3. The process according to claim 1, wherein in the alkylation step the amount of water is at least 0.6 mol per mol of 2-butanone.

4. The process according to claim 1, wherein in the alkylation step the amount of water ranges from 0.7 to 0.9 mol per mol of 2-butanone.

5. The process according to claim 1, wherein in the alkylation step the amount of potassium carbonate or potassium hydroxide ranges from 3 to 3.5 mol per mol of the benzothiazepine derivative of formula (II) or salt thereof.

6. The process according to claim 1, wherein in the alkylation step the amount of 2-butanone ranges from 1.3 to 1.9 times the amount by weight of the benzothiazepine derivative of formula (II) or salt thereof.

7. The process according to claim 1, wherein in the alkylation step the amount of 2-(dimethylamino)ethyl halide or salt thereof ranges from 1.05 to 1.18 mol per mol of the benzothiazepine derivative of formula (II) or salt thereof.

8. The process according to claim 1, wherein in the alkylation step the 2-(dimethylamino)ethyl halide or salt thereof is 2-(dimethylamino)-ethyl chloride or a salt thereof.

9. The process according to claim 1, wherein the process is conducted for a time period ranging from 50 minutes to 2.5 hours.

10. The process of claim 9, wherein the process further includes the addition of supplemental water to the reaction mixture.

11. The process of claim 10, wherein after reaction the aqueous phase is separated from the organic product containing phase.

12. The process of claim 11, wherein 2-butanone is removed from the organic product containing phase.

13. A process according to claim 1, wherein the benzothiazepine derivative is a cis-(+)-3-acetoxy-5-[2-(dimethylamino)ethyl]-2,3-dihydro-2-(4-methoxyphenyl)-1,5-benzothiazepin-4(5H)-one of the formula (Ia)

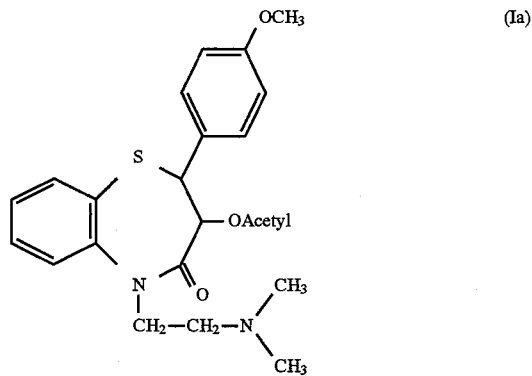

or of a pharmaceutically acceptable salt thereof.

* * * * *